United States Patent [19]

Shaw

[11] Patent Number: 4,994,150

[45] Date of Patent: Feb. 19, 1991

[54] PROCESS FOR THE PURIFICATION OF ESTERS OF MERCAPTO ACIDS

[75] Inventor: James E. Shaw, Bartlesville, Okla.

[73] Assignee: Phillips Petroleum Company, Bartlesville, Okla.

[21] Appl. No.: 397,935

[22] Filed: Aug. 24, 1989

[51] Int. Cl.$^5$ .................... B01D 3/34; C07C 32/04
[52] U.S. Cl. ............................ 203/14; 203/29; 203/33; 203/39; 203/51; 203/68; 203/69; 560/147
[58] Field of Search .................. 203/14, 39, 29, 33, 203/51, 68, 69, 43; 560/147

[56] References Cited

U.S. PATENT DOCUMENTS

| | | | |
|---|---|---|---|
| 3,404,175 | 10/1968 | Mercier | 203/14 |
| 3,414,485 | 12/1968 | Speed | 203/DIG. 21 |
| 3,465,057 | 9/1969 | Cameron et al. | 560/147 |
| 3,663,624 | 5/1972 | Jones | 203/14 |
| 4,185,155 | 1/1980 | Bader et al. | 560/152 |
| 4,342,627 | 8/1982 | Cane et al. | 203/68 |
| 4,889,950 | 12/1989 | Bott et al. | 560/147 |

FOREIGN PATENT DOCUMENTS

| | | | |
|---|---|---|---|
| 270063 | 7/1989 | German Democratic Rep. | 560/147 |
| 1173165 | 12/1969 | United Kingdom | 560/147 |

OTHER PUBLICATIONS

Encyclopedia of Chemical Technology, vol. 9, 1980, pp. 291-297.
Inorganic Anal. Chem., vol. 89, 1978, Abstract 122420v, Synthesis of Thioglycolic Acid Esters and Their Use in Analytical Chemistry.

Primary Examiner—Wilbur Bascomb
Attorney, Agent, or Firm—Richmond, Phillips, Hitchcock & Umphlett

[57] ABSTRACT

The present invention provides a process to recover esters of mercapto acids from solutions containing water by mixing an extraction mixture comprising cycloalkane, arene, and an aqueous inorganic salt solution with an ester of mercapto acid and water solution followed by separating and distilling the resultant organic phase to recover the ester of mercapto acid.

13 Claims, No Drawings

PROCESS FOR THE PURIFICATION OF ESTERS OF MERCAPTO ACIDS

FIELD OF THE INVENTION

This invention relates to a process for the purification of esters of mercapto acids from a solution containing water.

BACKGROUND OF THE INVENTION

Mercapto acids are generally esterified by heating mercapto acids in a reaction mixture containing an alcohol, a strong acid catalyst, and optionally, a solvent.

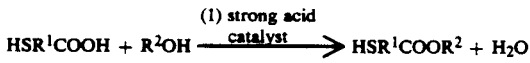

$$\text{HSR}^1\text{COOH} + \text{R}^2\text{OH} \xrightarrow{\text{(1) strong acid catalyst}} \text{HSR}^1\text{COOR}^2 + \text{H}_2\text{O}$$

If excess alcohol (~3 mole equivalents) is used, this reaction will usually yield approximately 95% ester in a crude reaction mixture with the starting materials and water (which is formed as a byproduct). Unfortunately, only a 65% yield of ester can be purified from this crude reaction mixture by conventional means such as distillation. The 30% loss of yield of ester appears to be the result of hydrolysis which occurs during the distillation process.

As the distillation is performed on the crude reaction mixture the first material removed is the excess short chain alcohol. Removing the short chain alcohol shifts the equilibrium of the reaction towards favoring the hydrolysis of the ester back to the mercapto acid and alcohol starting materials. If a method of removing the water from the crude reaction mixture prior to distillation could be discovered, the hydrolysis of the ester could be avoided.

Various methods have been tried to remove the water from the crude reaction mixture set forth above, such as the addition of drying agents or the extraction of water utilizing simple organic solvents. Neither of these methods has proven to be satisfactory. On a commercial scale it is economically unfeasible to use conventional drying agents to remove water. Extracting the water utilizing simple organic solvents such as toluene or chloroform has also been tried but with limited success. The simple solvent systems either leave too much water in the organic phase (which results in hydrolysis of the ester) or leave too much of the ester produced in the aqueous phase which is to be discarded.

Thus, it would be a significant contribution to the art to develop an alternative purification process for recovering substantially water free esters of mercapto acids.

Additionally, it would be particularly advantageous to provide a process for recovering esters of mercapto acids from a reaction mixture containing water which allows for recovery of substantially all of the ester present in said reaction mixture.

It would also be advantageous if a purification process for recovering esters of mercapto acids could be developed which economically provided for the recovery of a substantially water free ester.

It is an object of this invention to provide an alternative purification process for the recovery of substantially water-free esters of mercapto acids.

It is also an object of this invention to provide a process for recovering substantially all of the ester of a mercapto acid present from a reaction mixture containing water.

It is a further object of this invention to provide an economical process for recovering a substantially water free ester of a mercapto acid.

Other aspects, objects, and several advantages of this invention will be apparent from this specification.

SUMMARY OF THE INVENTION

In accordance with the present invention I have discovered a process for the recovery of esters of mercapto acids from a first mixture containing ester and water comprising the following steps:

(a) mixing said first mixture with an effective amount of cycloalkane, arene, and an aqueous inorganic salt to form a second mixture;

(b) allowing said second mixture to separate into an organic phase and an aqueous phase, retaining the organic phase; and (c) distilling said organic phase in a suitable manner to recover said ester.

DETAILED DESCRIPTION OF THE INVENTION

The present invention provides a process for the purification of esters of mercapto acids from solutions containing water as a component.

Esters of mercapto acids are usually synthesized by the following reaction:

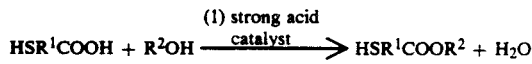

$$\text{HSR}^1\text{COOH} + \text{R}^2\text{OH} \xrightarrow{\text{(1) strong acid catalyst}} \text{HSR}^1\text{COOR}^2 + \text{H}_2\text{O}$$

If excess alcohol (~3 mole equivalents) is used, the crude reaction mixture under appropriate reaction conditions will yield about 95% ester. In this reaction $R^1$ may be a methylene, polymethylene, or alkyl substituted methylene or polymethylene containing a total of 1–20 carbon atoms and $R^2$ may be methyl or ethyl. Since the equilibrium constant of this reaction is very close to one (1) when equimolar amounts of alcohol and mercapto acid are used, care must be taken in handling the resultant reaction mixture to avoid the hydrolysis of the ester back to the mercapto acid and alcohol starting materials. Consequently, the water present in the resultant reaction mixture or any mixture must be removed carefully to avoid hydrolysis.

Esters of mercapto acids can be recovered from mixtures with water by mixing suitable esters including but not limited to esters selected from the group consisting of methyl thioglycolate (methyl mercaptoacetate), ethyl thioglycolate, methyl 3-mercaptopropionate, and ethyl 3-mercaptopropionate with an effective amount of cycloalkane, arene, and an aqueous alkali salt.

Suitable cycloalkanes for the practice of the present invention include cycloalkanes selected from the group consisting of cyclohexane, methyl substituted cyclohexanes, decalin, and combinations of any two or more thereof. Cyclohexane is the preferred cycloalkane for the practice of the present invention. The amount of cycloalkane to be employed in the present invention can range from about 0.1 to about 10 volume per volume of ester of mercapto acid and preferably be about 1 volume per volume of ester.

Suitable arenes for the practice of the present invention include arenes selected from the group consisting of toluene, benzene, ethylbenzene, xylenes, tetralin, and combinations thereof. Toluene is the preferred arene for the practice of the present invention. The amount of arene utilized in the practice of the present invention can range from about 0.1 to about 10 volume of ester and preferably will be about 0.5 volume per volume ester.

The concentration of aqueous inorgainc salt used in the present invention may range from about 1 to about 30 weight percent of the aqueous solution and preferably about 22 weight percent of the aqueous solution. The amount of aqueous inorganic salt employed can range from about 0.1 to about 10 volume per volume of ester of mercapto acid and preferably the amount of aqueous inorganic salt employed will range from about 0.5 to about 1.0 volume per volume of ester. Inorganic salts suitable for the practice of the present invention include, but are not limited to, inorganic salts selected from the group consisting of sodium chloride, sodium bromide, sodium sulfate, potassium chloride, ammonium chloride, and combinations of any two or more thereof. The preferred inorganic salt for the practice of the present invention is sodium chloride. The most preferred combination of cycloalkane, arene and inorganic salt for the practice of the present invention is the combination of cyclohexane, toluene, and sodium chloride.

The order of addition of the cycloalkane, arene, and aqueous inorganic salt to the ester and water solution is not critical to the practice of this invention, and any convenient order of addition may be adopted.

The cycloalkane, arene, and aqueous inorganic salt should be mixed with the ester and water-containing solution by any means known to those skilled in the art which provides for thorough mixing of these components which preferably does not promote the formation of emulsions. The mixing time of these components is not critical and can range from about a 5 seconds to about 5 hours. The preferred mixing time is from about 1 minute to about 3 minutes. The temperature at which the mixing of these components occurs is not critical and can generally be described as temperatures at which all the components are readily flowing liquids such as in the range of about 0° C to about 40° C.

After the cycloalkane, arene, aqueous inorganic salt, ester, and water are mixed together, the solution so formed will separate into two phases. One phase will be an organic phase which contains the ester, cycloalkane, arene, and a minor amount of water. The organic phase may be separated from the other phase present by any suitable technique known to those of skill in the art including, but not limited to decanting said organic phase.

The organic phase may then be subjected to distillation by suitable distillation techniques known to those skilled in the art including but not limited to fractional distillation. The ester can be recovered during distillation by monitoring and collecting the ester fraction.

The following non-limiting examples are provided to further illustrate the practice of the present invention.

EXAMPLE I

A synthetic crude methyl thioglycolate reaction product was prepared as follows. 100.8 g (85 ml) of methyl thioglycolate, 4.6 g of thioglycolic acid, 17.1 g of water, and 65.7 g of methanol were added to a 500 ml separatory flask. To remove water the reaction product was extracted with 42.5 ml (36.8 g) toluene and 65.9 ml of saturated aqueous sodium chloride solution. After phase separation, the organic phase (bottom) weighed 135 g and contained 2.55% water which meant 20% of the water that was originally in the crude reaction product was still with the methyl thioglycolate phase.

This Example demonstrates that toluene by itself is not effective in removing water from a mixture of methyl thioglycolate and water.

EXAMPLE II

A synthetic crude methyl thioglycolate reaction product was prepared as follows. 100.8 g (85 ml) of methyl thioglycolate, 4.6 g of thioglycolic acid, 17.1 g of water, and 65.7 g of methanol were added to a 500 ml separatory funnel. To remove water prior to distillation the reaction product was extracted with a mixture of 85 ml cyclohexane (65.25 g), 42.5 ml toluene (36.53 g), and 67.9 ml of a 22% aqueous NaCl solution. After phase separation, the organic layer (top) weighed 199.53 g and the aqueous layer (bottom) weighed 166.91 g. Analysis of the organic layer by gas chromatography showed that it contained 94.0% of the methyl thioglycolate, 3.1% of the methanol, 15.0% of the thioglycolic acid, and 7.8% of the water that was originally in the crude reaction product. The organic layer was then distilled on a high efficiency metal packed column, and resulted in 92% of the methyl thioglycolate being recovered that was originally in the crude reaction product. The purity was ~99%.

This Example demonstrates that utilizing cyclohexane, toluene and an aqueous alkali salt solution that a substantially water free methyl thioglycolate can be produced.

The foregoing examples have been provided merely to illustrate the practice of the present invention and should not be read as limitations on the scope of the invention or the appended claims in any way.

Reasonable variations and modifications, not departing from the essence and spirit of the invention, are contemplated to be within the scope of patent protection desired and sought.

That which is claimed is:

1. A process for the recovery of esters of mercapto acids from a first mixture containing an ester of mercapto acid and water comprising the following steps:
   (a) mixing said first mixture with an effective amount of cycloalkane, arene, and an aqueous inorganic salt to form a second mixture;
   (b) allowing said second mixture to separate into an organic phase and an aqueous phase, retaining the organic phase; and
   (c) distilling said organic phase in a suitable manner to recover said ester.

2. The process of claim 1 wherein said cycloalkane is provided in the range from about a 0.1 to about 10 volume of cycloalkane per volume of ester.

3. The process of claim 2 wherein the cycloalkane is selected from the group consisting of cyclohexane, methyl substituted cyclohexane, decalin and combinations of any two or more thereof.

4. The process of claim 2 wherein the cycloalkane is cyclohexane.

5. The process of claim 1 wherein said arene is selected from the group consisting of toluene, benzene, ethylbenzene, xylenes, tetralin, and combinations thereof, and is provided in the range of from about a 0.1 to about 10 volume of arene per volume of ester.

6. The process of claim 5 wherein the arene is toluene.

7. The process of claim 1 wherein said aqueous inorganic salt is provided in a concentration range of from approximately 1 to approximately 30 weight percent and in the range of from about 0.1 to about 10 volume of aqueous inorganic salt per volume of ester.

8. The process of claim 7 wherein the inorganic salt is selected from the group consisting of sodium chloride, sodium bromide, sodium sulfate, potassium chloride, ammonium chloride, and combinations of any two or more thereof.

9. The process of claim 7 wherein the inorganic salt is sodium chloride.

10. A process for the recovery of esters of mercapto acids from a mixture containing an ester of mercapto acid and water comprising the following steps:
   (a) mixing said first mixture with an effective amount of cyclohexane in the range of from about 0.1 to about 10 volume cyclohexane per volume of ester, toluene in the range of from about 0.1 to about 10 volume toluene per volume of ester, and an aqueous inorganic salt in a concentration ranging from about 1 to about 30 weight percent and in the range of from about a 0.1 to about 10 volume of aqueous inorganic salt per volume of ester to form a second mixture;
   (b) allowing said second mixture to separate into an organic phase and an aqueous phase, retaining the organic phase; and
   (c) distilling said organic phase in a suitable manner to recover said ester.

11. The process of claim 10 wherein the inorganic salt is selected from the group consisting of sodium chloride, sodium bromide, sodium sulfate, potassium chloride, and ammonium chloride.

12. The process of claim 10 wherein the inorganic salt is sodium chloride.

13. The process of claim 10 wherein the amount of cyclohexane mixed with said first mixture is about 1 volume per volume of ester; the amount of toluene mixed with said first mixture is about 0.5 volume per volume of ester; and the aqueous inorganic salt is sodium chloride in a concentration of about 22 weight percent provided in the range of about 0.5 to about 1.0 volume per volume of ester.

* * * * *